United States Patent
Kawanaka et al.

(10) Patent No.: US 12,394,511 B2
(45) Date of Patent: Aug. 19, 2025

(54) METHODS AND SYSTEMS FOR REMOTE ANALYSIS OF MEDICAL IMAGE RECORDS

(71) Applicant: FUJIFILM MEDICAL SYSTEMS U.S.A., INC., Morrisville, NC (US)

(72) Inventors: Tatsuo Kawanaka, Tokyo (JP); Keiji Sugihara, Cary, NC (US)

(73) Assignee: FUJIFILM HEALTHCARE AMERICAS CORPORATION, Lexington, MA (US)

( * ) Notice: Subject to any disclaimer, the term of this patent is extended or adjusted under 35 U.S.C. 154(b) by 439 days.

(21) Appl. No.: 16/686,571

(22) Filed: Nov. 18, 2019

(65) Prior Publication Data

US 2021/0151169 A1    May 20, 2021

(51) Int. Cl.
  *G16H 30/20*    (2018.01)
  *G16H 10/60*    (2018.01)
  *G16H 50/20*    (2018.01)

(52) U.S. Cl.
  CPC .............. *G16H 30/20* (2018.01); *G16H 10/60* (2018.01); *G16H 50/20* (2018.01)

(58) Field of Classification Search
  CPC ......... G16H 30/20; G16H 10/60; G16H 50/20
  See application file for complete search history.

(56) References Cited

U.S. PATENT DOCUMENTS

| | | | | |
|---|---|---|---|---|
| 2003/0229520 | A1* | 12/2003 | Wise | G16H 40/67 705/50 |
| 2004/0025154 | A1* | 2/2004 | Sedlack | G06F 8/63 717/168 |
| 2004/0086162 | A1* | 5/2004 | Doi | G06T 7/0012 382/190 |
| 2006/0026040 | A1* | 2/2006 | Reeves | G16H 30/20 382/128 |
| 2007/0237372 | A1* | 10/2007 | Chen | G06V 10/7515 382/128 |

(Continued)

FOREIGN PATENT DOCUMENTS

| | | | |
|---|---|---|---|
| EP | 3 483 895 A1 | 5/2019 | |
| EP | 3 483 897 A1 | 5/2019 | |

(Continued)

OTHER PUBLICATIONS

International Search Report and Written Opinion mailed Feb. 17, 2021 in International Application No. PCT/US20/60705.

*Primary Examiner* — Peter H Choi
*Assistant Examiner* — Aaisha Abdullah
(74) *Attorney, Agent, or Firm* — Baker Botts L.L.P.

(57) ABSTRACT

A method for remote analysis of one or more medical image records, including: receiving, at a workstation of a first user, a first medical image record; comparing the first medical image record with a standard image set to identify a similarity between the first medical image record and the standard image set; calculating, if the similarity is above a threshold, a delta between the first medical image record and the standard image set by comparing the first medical image record and the standard image set; transferring the delta from the workstation of the first user and to one or more computing devices; reconstructing the first medical image record by combining the delta with the standard image set having a copy of the standard image set; and analyzing the first medical image record.

23 Claims, 6 Drawing Sheets

(56) References Cited

U.S. PATENT DOCUMENTS

| | | | |
|---|---|---|---|
| 2007/0238954 A1* | 10/2007 | White | A61B 8/481 600/407 |
| 2008/0037876 A1 | 2/2008 | Galperin | |
| 2008/0130967 A1 | 6/2008 | Wang et al. | |
| 2009/0028403 A1 | 1/2009 | Bar-Aviv et al. | |
| 2009/0245624 A1* | 10/2009 | Hamanaka | G06V 40/172 382/209 |
| 2011/0150302 A1* | 6/2011 | Moriyama | G06F 16/583 382/118 |
| 2013/0051667 A1* | 2/2013 | Deng | G06V 10/7515 382/218 |
| 2015/0172681 A1* | 6/2015 | Kim | G16H 30/40 382/128 |
| 2015/0222931 A1* | 8/2015 | Rozzi | H04N 19/593 382/236 |
| 2016/0364529 A1* | 12/2016 | Li | G16H 40/20 |
| 2018/0293772 A1* | 10/2018 | Akahori | G06T 11/60 |
| 2019/0043611 A1 | 2/2019 | Saalbach et al. | |
| 2019/0051398 A1 | 2/2019 | Zankowski et al. | |
| 2019/0053855 A1 | 2/2019 | Siemionow et al. | |
| 2019/0108441 A1* | 4/2019 | Thibault | G01N 23/046 |
| 2019/0156241 A1 | 5/2019 | Hughes | |
| 2019/0163949 A1 | 5/2019 | Park et al. | |
| 2019/0171467 A1 | 6/2019 | Hermosillo et al. | |
| 2019/0172581 A1* | 6/2019 | Zlotnick | G06N 3/08 |
| 2019/0188848 A1 | 6/2019 | Madani et al. | |
| 2019/0189266 A1 | 6/2019 | Stoval, III et al. | |
| 2019/0189267 A1 | 6/2019 | Stoval, III et al. | |
| 2019/0361079 A1* | 11/2019 | Takeshima | G01R 33/4824 |
| 2020/0019823 A1* | 1/2020 | Wang | G06N 3/0454 |
| 2020/0058388 A1* | 2/2020 | Vincent | G16H 30/20 |
| 2021/0056675 A1* | 2/2021 | Higa | G06V 30/19147 |
| 2021/0134460 A1* | 5/2021 | Ratner | G06T 7/0014 |

FOREIGN PATENT DOCUMENTS

| | | |
|---|---|---|
| JP | 2003-38476 A | 2/2003 |
| JP | 2009-279342 A | 12/2009 |
| JP | 2017-108852 A | 6/2017 |
| JP | 2018-61771 A | 4/2018 |

* cited by examiner

METHODS AND SYSTEMS FOR REMOTE ANALYSIS OF MEDICAL IMAGE RECORDS

BACKGROUND

1. Field of Disclosed Subject Matter

The disclosed subject matter is directed to systems and methods for remote analysis of digital records, for example, medical image records. Particularly, portions of the medical image records can be transferred to a cloud-based artificial intelligence ("AI") medical diagnostic engine for analysis.

2. Description of Related Art

Utilizing AI for medical diagnostics is becoming more popular and important. AI medical diagnostic engines (also referred to herein as "AI engines") can receive and process one or more medical images to perform the diagnosis. While images can be stored in a variety of formats, a common format for image storage is Digital Imaging and Communications in Medicine ("DICOM"). DICOM is a standard in which, among other things, medical images and associated meta-data can be communicated from imaging modalities (e.g., x-ray (or x-rays' digital counterparts: computed radiography (CR) and digital radiography (DR)), computed tomography (CT), and magnetic resonance imaging (MRI) apparatuses) to client devices and/or remote storage.

AI engines can typically train themselves using a large amount of data and can work faster than normal diagnostic applications. The AI engines can continue to be improved and refined even after the first use. When AI engines are stored on individual computers (i.e., locally), every time an AI engine is improved, the AI engine must be upgraded at each location and on each computer running the AI engine. Accordingly, it can be beneficial to deploy an AI engine on a cloud (i.e., remote from each individual workstation), where the AI engine can be accessed by multiple users at different locations and where the AI engine can be more easily upgraded.

However, implementing AI engines on a cloud can present several problems. First, the size of the medical images that need to be uploaded to the cloud for review by the AI engines can be large. This can take a lot of time, which can be a problem for medical situations where speed is critical (e.g., diagnosing a potential stroke). Second, uploading medical images to the cloud can raise security issues, even if personal data is removed before the images are uploaded.

Accordingly, there is a need for improved systems and methods for facilitating remote analysis of medical image records. Particularly, there is a need to reduce the amount of data that needs to be uploaded to the cloud and there is a need to improve security.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to systems and methods for remote analysis of one or more medical image records. For example, a method for remote analysis of one or more medical image records includes receiving, at a workstation of a first user, a first medical image record; comparing, at the workstation of the first user, the first medical image record with a standard image set to identify a similarity between the first medical image record and the standard image set; calculating, if the similarity is above a threshold and at the workstation of the first user, a delta between the first medical image record and the standard image set by comparing the first medical image record and the standard image set; transferring the delta from the workstation of the first user and to one or more computing devices having a copy of the standard image set; reconstructing, by the one or more computing devices, the first medical image record by combining the delta with the standard image set; and analyzing, by the one or more computing devices, the first medical image record.

In accordance with the disclosed subject matter the first medical image record can include one or more DICOM Service-Object Pair instances. The standard image set can include one or more standard images. The standard image set can include a plurality of standard images of an anatomical feature. The method can include generating the standard image set using a plurality of images of the anatomical feature. The plurality of images can include normal and abnormal images of the anatomical feature. The method can include providing an alert to the user if the similarity is below a threshold.

In accordance with the disclosed subject matter, comparing the first medical image record with the standard image set can include determining that the first medical image record and the standard image set each correspond with a similar anatomical feature. Analyzing the first medical image record can include determining a medical diagnosis. The method can include sending an alert to the workstation of the first user if the medical diagnosis is abnormal. Analyzing the first medical image record can include using an artificial intelligence ("AI") engine stored on the one or more computing devices. The method can include sending, from the one or more computing devices and to the workstation of the first user, the analysis of the first medical image record.

In accordance with the disclosed subject matter, one or more computer-readable non-transitory storage media embodying software are provided. The software can be operable when executed to: receive, at a workstation of a first user, a first medical image record; compare, at the workstation of the first user, the first medical image record with a standard image set to identify a similarity between the first medical image record and the standard image set; identify, if the similarity is above a threshold and at the workstation of the first user, a delta between the first medical image record and the standard image set by comparing the first medical image record and the standard image set; transfer the delta from the workstation of the first user and to one or more computing devices having a copy of the standard image set; reconstruct, by the one or more computing devices, the first medical image record by combining the delta with the standard image set; and analyze, by the one or more computing devices, the first medical image record.

In accordance with the disclosed subject matter, a system including one or more processors; and a memory coupled to the processors including instructions executable by the processors are provided. The processors can be operable when executing the instructions to: receive, at a workstation of a first user, a first medical image record; compare, at the workstation of the first user, the first medical image record with a standard image set to identify a similarity between the first medical image record and the standard image set; identify, if the similarity is above a threshold and at the workstation of the first user, a delta between the first medical image record and the standard image set by comparing the first medical image record and the standard image set; transfer the delta from the workstation of the first user and to one or more computing devices having a copy of the standard image set; reconstruct, by the one or more computing devices, the first medical image record by combining the delta with the standard image set; and analyze, by the one or more computing devices, the first medical image record.

In accordance with the disclosed subject matter, a system for remote analysis of one or more medical image records is provided. The system can include a workstation having a processor, including a pre-processing AI engine for processing a first medical image record, and a memory storing a first copy of a standard image set. The system can further include one or more computing devices operationally coupled to the workstation, the one or more computing devices including an AI engine, and an AI engine storage storing a second copy of the standard image set.

In accordance with the disclosed subject matter, the workstation further can include a transceiver for sending a delta to the server. The delta can be calculated by the pre-processing AI engine by comparing the first medical image record and the first copy of the standard image set. The workstation can include a graphical user interface. The one or more computing devices can include a server processor. The server processor can be configured to combine the delta with the second copy of the standard image set to reconstruct the first medical image record. The system can include an imaging modality operationally coupled to the workstation to send the first medical image record from the imaging modality to the workstation.

DRAWINGS

DETAILED DESCRIPTION

Reference will now be made in detail to the various exemplary embodiments of the disclosed subject matter, exemplary embodiments of which are illustrated in the accompanying drawings. The methods and systems described herein can be used for remote analysis of one or more medical image records, such as medical records stored on a Picture Archiving and Communication Systems ("PACS"). A variety of records are suitable for use by the present disclosure and records can be stored in any system, for example a Vendor Neutral Archive ("VNA"). As used in the description and the appended claims, the singular forms, such as "a," "an," "the," and singular nouns, are intended to include the plural forms as well, unless the context clearly indicates otherwise.

Figure 1:
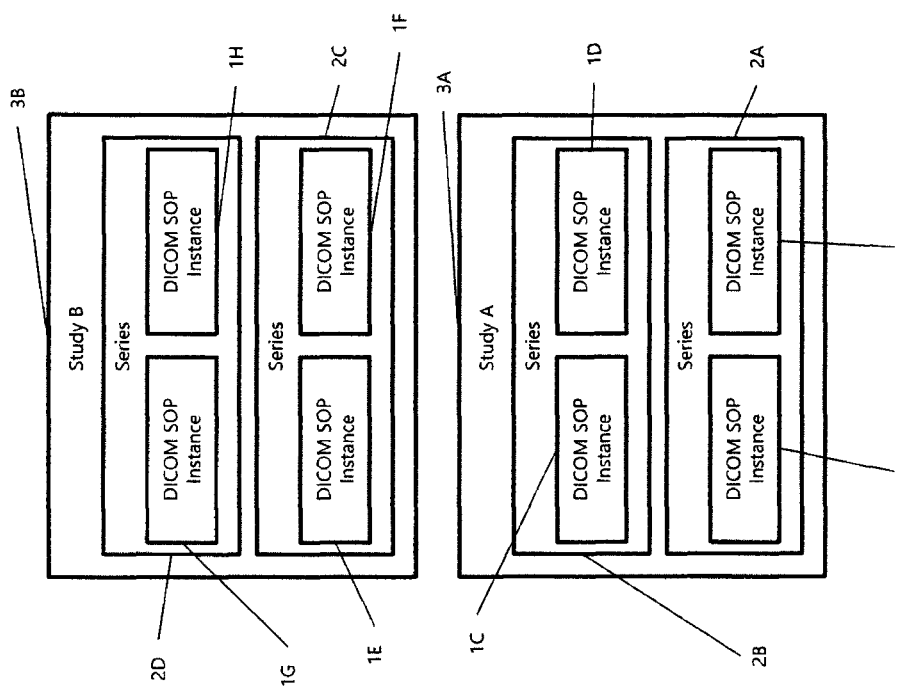
FIG. 1 shows a hierarchy of medical image records that can be viewed in accordance with the disclosed subject matter.

For purpose of illustration and not limitation, the systems and methods are described herein with respect to transferring and analyzing medical image records (referred to herein as "medical image records" or "records"), specifically, DICOM records, stored on a PACS. For example, and with reference to FIG. 1 for purpose of illustration and not limitation, as referred to herein a medical image record can include a single DICOM Service-Object Pair ("SOP") Instance (also referred to as "DICOM Instance," "DICOM image," and "image") 1 (e.g., 1A-1H), one or more DICOM SOP Instances 1 in one or more Series 2 (e.g., 2A-D), one or more Series 2 in one or more Studies 3 (e.g., 3A, 3B), and one or more Studies 3.

Figure 2:
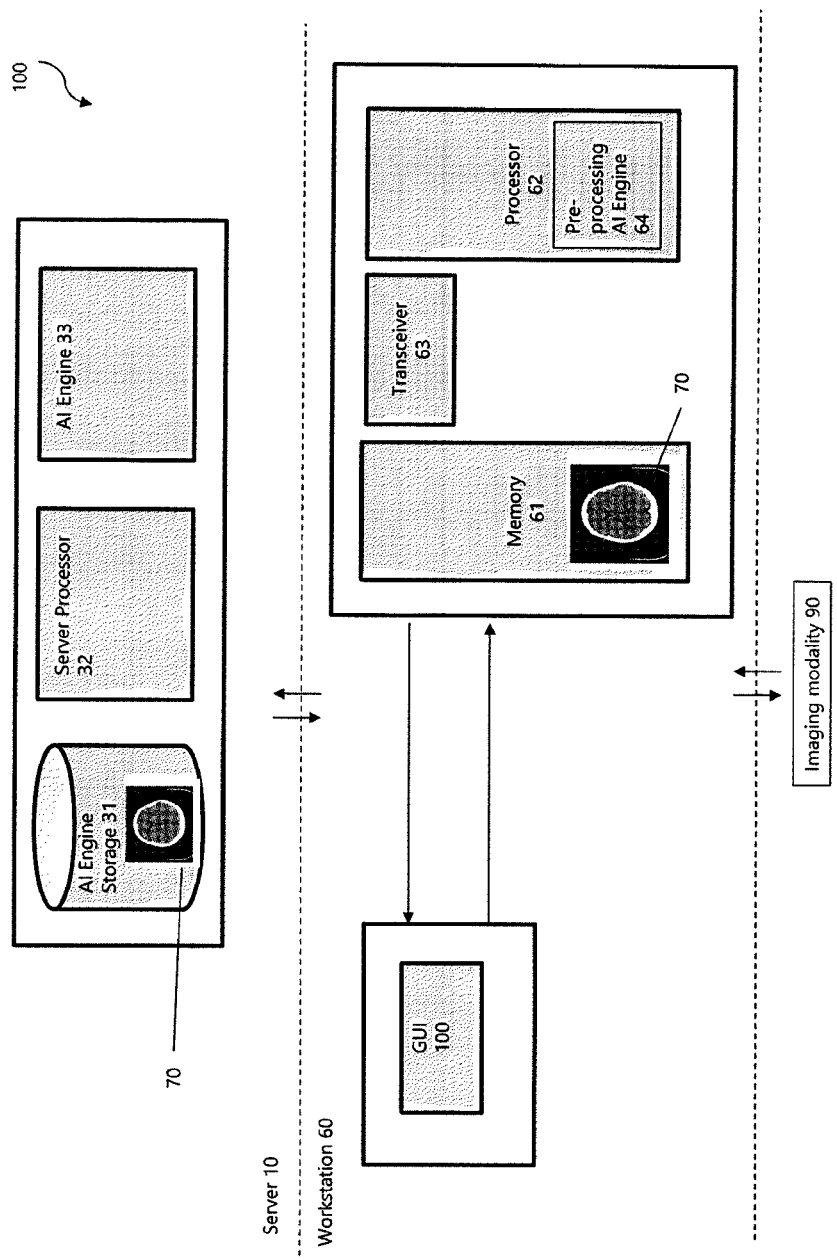
FIG. 2 shows the architecture of a system for remote analysis of one or more medical image records accordance with the disclosed subject matter.

Referring to FIG. 2 for purpose of illustration and not limitation, the disclosed system 100 can include one or more computing devices defining a server 10, a user workstation 60, and an imaging modality 90. In accordance with the disclosed subject matter, system 100 can be configured for remote analysis of one or more medical image records. The user workstation 60 can be coupled to the server 10 by a network. The network, for example, can be a Local Area Network ("LAN"), a Wireless LAN ("WLAN"), a virtual private network ("VPN"), or any other network that allows for any radio frequency or wireless type connection. For example, other radio frequency or wireless connections can include, but are not limited to, one or more network access technologies, such as Global System for Mobile communication ("GSM"), Universal Mobile Telecommunications System ("UMTS"), General Packet Radio Services ("GPRS"), Enhanced Data GSM Environment ("EDGE"), Third Generation Partnership Project ("3GPP") Technology, including Long Term Evolution ("LTE"), LTE-Advanced, 3G technology, Internet of Things ("IOT"), fifth generation ("5G"), or new radio ("NR") technology. Other examples can include Wideband Code Division Multiple Access ("WCDMA"), Bluetooth, IEEE 802.11b/g/n, or any other 802.11 protocol, or any other wired or wireless connection. Medical image records can be transferred between the server side 10 and workstation 60, and can be rendered at the workstation 60. More information on downloading and rendering medical images can be found in U.S. application Ser. No. 16/450,477, which is incorporated by reference herein.

Workstation 60 can take the form of any known client device. For example, workstation 60 can be a computer, such as a laptop or desktop computer, a personal data or digital assistant ("PDA"), or any other user equipment or tablet, such as a mobile device or mobile portable media player. Server 10 can be a service point which provides processing, database, and communication facilities. For example, the server can include dedicated rack-mounted servers, desktop computers, laptop computers, set top boxes, integrated devices combining various features, such as two or more features of the foregoing devices, or the like. Servers can vary widely in configuration or capabilities, but can include one or more processors, memory, and/or transceivers. A server can also include one or more mass storage devices, one or more power supplies, one or more wired or wireless network interfaces, one or more input/output interfaces, and/or one or more operating systems.

The Workstation 60 can communicate with imaging modality 90 either directly (e.g., through a hard wired connection) or remotely (e.g., through a network described above) via a PACS. The imaging modality 90 can be any medical imaging modality that can provide images that can be analyzed by an AI engine, including, for example, x-ray (or x-ray's digital counterparts: computed radiography (CR) and digital radiography (DR)), mammogram, tomosynthesis, computerized tomography (CT), magnetic resonance image (MRI), positron emission tomography (PET) and ultrasound imaging devices.

A user can be any person authorized to access workstation 60, including any health professional, medical technician, or a patient. In some embodiments a user authorized to communicate with the PACS and/or a remote AI engine can have a username and/or password that can be used to login or access workstation 60.

Server 10 can include AI engine storage 31, server processor 32 and AI engine 33. Server processor 32 can be any hardware or software used to execute computer program instructions. These computer program instructions can be provided to a processor of a general purpose computer to alter its function to a special purpose, a special purpose computer, application-specific integrated circuit ("ASIC"), or other programmable digital data processing apparatus, such that the instructions, which execute via the processor of the client station or other programmable data processing apparatus, implement the functions/acts specified in the block diagrams or operational block or blocks, thereby transforming their functionality in accordance with embodiments herein. In accordance with the disclosed subject matter, the server processor 32 can be a portable embedded micro-controller or micro-computer. For example, server processor 32 can be embodied by any computational or data processing device, such as a central processing unit ("CPU"), digital signal processor ("DSP"), ASIC, programmable logic devices ("PLDs"), field programmable gate arrays ("FPGAs"), digitally enhanced circuits, or comparable device or a combination thereof. The server processor 32 can be implemented as a single controller, or a plurality of controllers or processors.

AI engine 33 can be any engine that can perform a medical diagnosis using AI. The AI engine can be developed (i.e., "trained") using one or more of deep learning, hierarchical learning, machine learning, decision tree learning, and inductive logic programming. Additionally or alternatively, AI engine 33 can be trained using tools or techniques for developing AI engines, such as TensorFlow, Keras, Microsoft Azure, Google Cloud Prediction API, or any similar tools. The AI engine 33 can use a neural network, for example, an artificial neural network, feedforward neural network, recurrent neural network, bidirectional recurrent neural network, hierarchical recurrent neural network, stochastic neural network, modular neural network, associative neural network, deep neural network, convolutional neural network, large memory storage and retrieval neural network, Bayesian network, or artificial neural networks, or any combination of these or similar AI arrangements. AI engine storage 31 can store medical image records to be analyzed by AI engine 33 and can also store a standard image set 70. The standard image set 70 can be developed by the AI engine 33, or by other smart systems. For example, standard image set 70 can be developed by a machine learning algorithm (for example a deep learning algorithm) by reviewing a large set of images. Standard image set 70 can include one or more standard images 71. For example, if the system 100 is intended to identify kidney disease, the standard image set 70 can be generated based on a review of e.g., hundreds or thousands of images kidneys including normal (healthy) and abnormal (diseased) kidneys. For example, to develop a standard image set 70 for CT images of the kidney, at least 5000 cases can be reviewed, with each case containing 50-200 images. Accordingly, at least 250,000 images may be reviewed in this example. Typically, the review of more images can result in an improved standard image set 70. The standard image set 70 can be generated as part of the learning process of the AI engine 33. The standard image set 70 can then include several standard images 71 which can be a set of generic images of kidneys. As another example, and not by way of limitation, if the AI engine 33 is configured for detecting brain strokes, the standard image set 70 can include a plurality of standard images 71 including brain images, such as CT brain scans. Because the standard image set 70 can be created using a large number of images, the standard image set 70 can account for differences in gender, age, origin, size variation, modality, brand of modality, image processing (e.g., W/L, zoom, or pan), image quality or other issues. Additionally or alternatively, the standard image set 70 can include images whose properties and characteristics are similar to one or more of the training images. Although this disclosure describes generating the standard image set 70 in a particular manner, this disclosure contemplates generating the standard image set 70 in any suitable manner.

The workstation 60 can receive and send one or more medical image records from server 10 or imaging modality 90 using transceiver 63. Transceiver 63 can, independently, be a transmitter, a receiver, or both a transmitter and a receiver, or a unit or device that can be configured both for transmission and reception. In other words, transceiver 63 can include any hardware or software that allows workstation 60 to communicate with server 10 and/or imaging modality 90. Transceiver 63 can be either a wired or a wireless transceiver. When wireless, the transceiver 63 can be implemented as a remote radio head which is not located in the device itself, but in a mast. While FIG. 2 only illustrates a single transceiver 63, workstation 60 can include one or more transceivers 63.

Medical image records received at workstation 60 can be cached in memory 61 of workstation 60. Memory 61 can be a non-volatile storage medium or any other suitable storage device, such as a non-transitory computer-readable medium or storage medium. For example, memory 61 can be a random-access memory ("RAM"), read-only memory ("ROM"), hard disk drive ("HDD"), erasable programmable read-only memory ("EPROM"), electrically erasable programmable read-only memory ("EEPROM"), flash memory or other solid-state memory technology. Memory 61 can also be a compact disc read-only optical memory ("CD-ROM"), digital versatile disc ("DVD"), any other optical storage, magnetic cassettes, magnetic tape, magnetic disk storage or other magnetic storage devices, or any other physical or material medium which can be used to tangibly store the desired information or data or instructions and which can be accessed by a computer or processor. Memory 61 can be either removable or non-removable.

Medical image records received by workstation 60 can be processed using one or more processors 62. Processor 62 can be any hardware or software used to execute computer program instructions. These computer program instructions can be provided to a processor of a general purpose computer to alter its function to a special purpose, a special purpose computer, ASIC, or other programmable digital data processing apparatus, such that the instructions, which execute via the processor of the client station or other programmable data processing apparatus, implement the functions/acts specified in the block diagrams or operational block or blocks, thereby transforming their functionality in accordance with embodiments herein. The processor 62 can be a portable embedded micro-controller or micro-computer. For example, processor 62 can be embodied by any computational or data processing device, such as a CPU, DSP, ASIC, PLDs, FPGAs, digitally enhanced circuits, or comparable device or a combination thereof. The processor 62 can be implemented as a single controller, or a plurality of controllers or processors. Processor 62 can include a pre-processing AI engine 64.

Memory 61 can include standard image set 70. The standard image set 70 stored on memory 61 is the same as the standard image set 70 stored on the AI engine storage 31 of the server 10. In other words, there is a copy of the standard image set 70 stored on both the workstation 60 and the server 10. Pre-processing AI engine 64 can use the standard image set 70 to process medical image records received at the workstation 60.

In operation, workstation 60 can receive one or more medical image records, for example a Series 2, to be analyzed. Pre-processing AI engine 63 can compare each DICOM SOP Instance 1 within Series 2 with each standard image 71 in standard image set 70. Pre-processing AI engine 63 can determine a similarity between each DICOM SOP Instance 1 and each standard image 71. Similarity can be determined, for example, using a pixel-by-pixel comparison between the DICOM SOP Instance 1 and the standard image 71. A similarity score can be calculated for each DICOM SOP Instance 1 and the DICOM SOP Instance 1 can be identified as similar if the similarity score is above a threshold. Factors that can be used in calculating the similarity score can include the gender, age, image position, image orientation, zoom of the image, the quality of the image, type (i.e., modality) of the image, the brand of the imaging modality 90, or any suitable feature of the image. As an example and not by way of limitation, if the system is intended to detect kidney disease, the standard image set 70 can contain images of all or portions of kidneys. Pre-processing AI engine 63 can identify DICOM SOP Instances 1 within series 2 that are similar to standard images 71 in the standard image set 70. For example, the standard images 71 and DICOM SOP Instances 1 can include images that have the same portion of a kidney. Identifying only certain DICOM SOP Instances 1 within Series 2 as similar can reduce the overall processing required. Although this disclosure describes identifying a similarity in a particular manner, this disclosure contemplates identifying a similarity in any suitable manner. If no DICOM SOP Instances 1 are identified as similar, an alert can be provided to the user, for example, on GUI 100. Pre-processing AI engine 63 can determine a delta 72 for each DICOM SOP Instance 1 that is identified as similar by comparing each DICOM SOP Instance 1 with at least one standard image 71. For example, the delta 72 can be calculated by subtracting a DICOM SOP Instance 1 from a standard image 71. The delta 72 for a given figure can include less data than the entire DICOM SOP Instance 1. Workstation 60 can transfer each delta 72 to the server 10, for example, using transceiver 63. If there is more than one standard image 71 in standard image set 72, workstation 60 can also send a reference for each delta 72 to identify which standard image 71 was used to create the delta 72. Server processor 32 can reconstruct each DICOM SOP Instance 1 that was identified as similar by combining each delta 72 with at least one standard image 71 from the standard image set 70 stored on the AI engine storage 31. Once the DICOM SOP Instances 1 to be evaluated have been recreated on the server 10, AI engine 33 can analyze the images 1. For example, the AI engine 33 can perform AI diagnostic analysis on the images 1. The results of the AI diagnostic analysis can be sent from the server 10 to the workstation 60. The results can be displayed on GUI 100. If the results of the diagnosis are abnormal or that there is an emergency, an alert can be sent to the workstation 60 for display on GUI 100.

Figure 3:
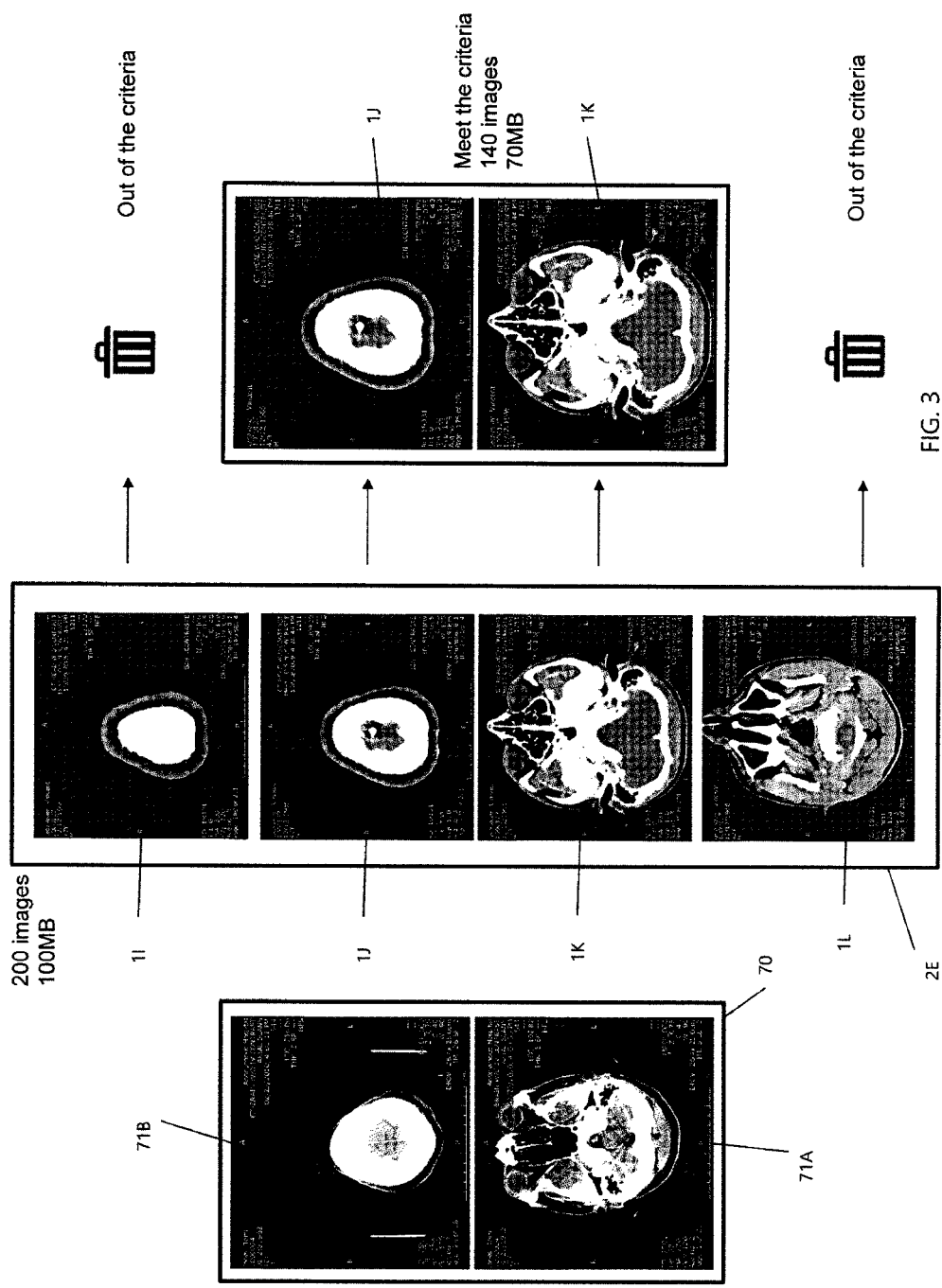
FIG. 3 shows exemplary medical image records and standard images in accordance with the disclosed subject matter.

With reference to FIGS. 2 and 3 for purpose of illustration and not limitation, system 100 can be configured to identify strokes. Accordingly, standard image set 70 can include at least two standard images 71 (only 71A, 71B are shown) of brains. The standard images 71 can be based on scans (e.g., CT scans) of, for example, thousands of normal and abnormal brains. Workstation 60 can receive Series 2E for analysis. Series 2E can include 200 DICOM SOP Instances 1 (only 1I, 1J, 1K, 1L are shown) and can include 100 MB of data. Pre-processing AI engine 63 compares each DICOM SOP Instance 1 to at least one standard image 71 in standard image set 70. Pre-processing AI engine 63 finds that DICOM SOP Instances 1I and 1L are not similar to the standard images 71, and therefore DICOM SOP Instances 1I and 1L are discarded. In contrast, pre-processing AI engine 63 finds that DICOM SOP Instances 1J and 1K are similar to at least one standard image 71. That is, DICOM SOP Instance 1J is similar to standard image 71B and DICOM SOP Instance 1K is similar to standard image 71A. Overall, pre-processing AI engine 63 identified 140 DICOM SOP Instances 1 that are considered similar (e.g., had a similarity score over a threshold or otherwise match the required criteria for further processing). The 140 DICOM SOP Instances 1 can include 70 MB of data—30 MB less than the 200 DICOM SOP Instances 1 that make up the entire Series 2E. Accordingly, performing the first test for similarity can reduce the number of images that need to be further analyzed and can therefore speed up the entire process. If one or more of the DICOM SOP Instances 1 are not similar to the standard images 71, an alert can be sent to the user. For example, an alert can be displayed on GUI 100. The alert can indicate that the DICOM SOP Instance 1 is not suitable for the AI engine 33 and therefore the DICOM SOP Instances 1 will not be pre-processed or sent to the server 10.

Figure 4:
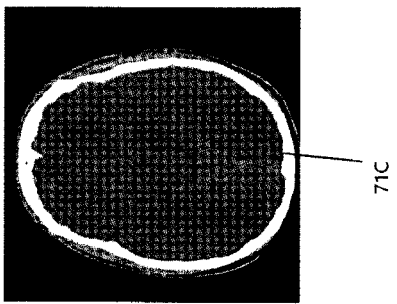
FIG. 4 illustrates how a delta can be calculated using a medical image record and a standard image, in accordance with the disclosed subject matter.
Figure 4:
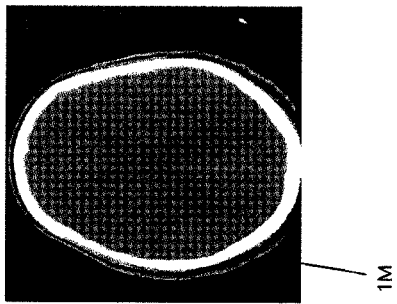
Figure 4:
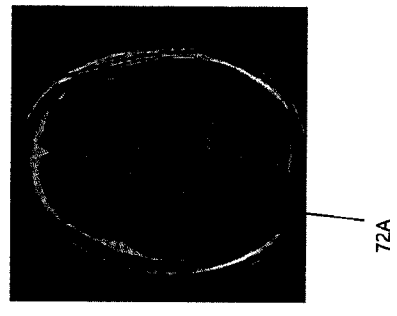

With reference to FIG. 4 for purpose of illustration and not limitation, pre-processing AI engine 63 compares standard image 71C to DICOM SOP Instance 1M to identify delta 72A. For example, delta 72A is calculated by adding or subtracting standard image 71C and DICOM SOP Instance 1M. For example, and not by way of limitation, the DICOM SOP Instance 1 can be subtracted from the standard image 71 that is most similar to the DICOM SOP Instance 1 to calculate delta 72. As noted above, the delta 71 can be sent from the workstation 60 to the server 10. The workstation 60 can also send a reference to the specific index number of the standard image 71 that was used to calculate the delta. For example, and with reference to FIG. 4 for purpose of illustration and not limitation, the workstation 60 can send information to server 10 that delta 72A was created using standard image 71C. Additionally or alternatively, pre-processing AI engine 63 can calculate a delta 72 and run a compression process. For example, and not by way of limitation, pre-processing AI engine 63 can compress delta 72A, which can further reduce data size. Alternatively or additionally, pre-processing AI engine 63 can compress the standard image 71C and the DICOM SOP Instance 1M, and then calculate a delta 72A therebetween. Although this disclosure describes calculating a delta in a particular manner, this disclosure contemplates calculating a delta in any suitable manner. Delta 72A can then be transferred to the server 10.

Figure 5:
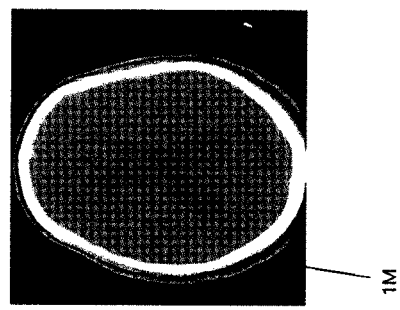
FIG. 5 illustrates how a medical image record can be calculated using a standard image and a delta, in accordance with the disclosed subject matter.
Figure 5:
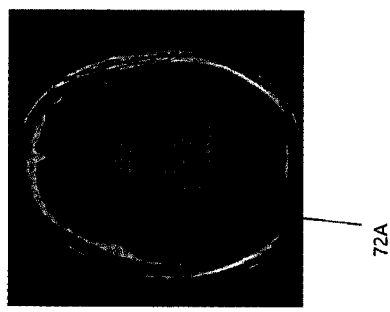
Figure 5:
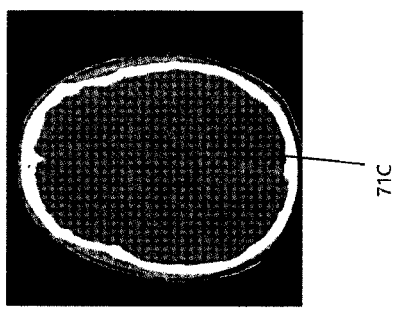

With reference to FIG. 5 for purpose of illustration and not limitation, server processor 32 can combine standard image 71C—which is stored on the server 10 at AI engine storage 31—with delta 72A—which was transferred from workstation 60, along with information regarding with which standard image 71 (e.g., specifically standard image 71C) the delta 72A should be combined—to recreate DICOM SOP Instance 1M. For example, DICOM SOP Instance 1M can be recreated by adding or subtracting standard image 71C and delta 72A. Additionally, decompression can be performed if compression was performed by pre-processing AI engine 63, as described above. For example, decompression can be performed if one or more of the DICOM SOP Instance 1M, standard image 71C, or delta 72A were initially compressed by pre-processing AI engine 63. Although this disclosure describes recreating medical image records in a particular manner, this disclosure contemplates recreating medical image records in any suitable manner. If server processor 32 encounters a problem recreating the image 71, an error message can be sent to workstation 60.

AI engine 33 can analyze the recreated DICOM SOP Instances 1. For example, the AI engine 33 can perform AI diagnostic analysis on the DICOM SOP Instances 1. The results of the AI diagnostic analysis can be sent from the server 10 to the workstation 60 and displayed on GUI 100. If determined to be necessary, an alert can be sent to the workstation 60. An alert can be sent, for example, if the analysis concludes that the patient is sick (abnormal) or if the analysis concludes that there is an urgent need for specific care. For example, if the AI diagnostic analysis concludes that the patient is having a stroke, an alert can be sent.

In accordance with the disclosed subject matter, only the delta 72 needs to be transferred to the server 10, because the DICOM SOP Instance 1 can be recreated using standard image set 70. Accordingly, less data needs to be transferred, because the delta 72 is smaller than the DICOM SOP Instance 1, and therefore the transfer of data from the workstation 60 to the server 10 can be faster. Furthermore, because only the delta 72 is transferred, the standard image set 70 acts as a key for recreating the DICOM SOP Instance 1. That is, each DICOM SOP Instance 1 cannot be recreated without the delta 72, and therefore the standard image set 70 is required to recreate and analyze the medical image records. This can increase security of transferring medical image records for remote analysis because third parties will need to acquire both the transferred delta 72 and the stored standard image set 70 to recreate the medical image records.

Figure 6:
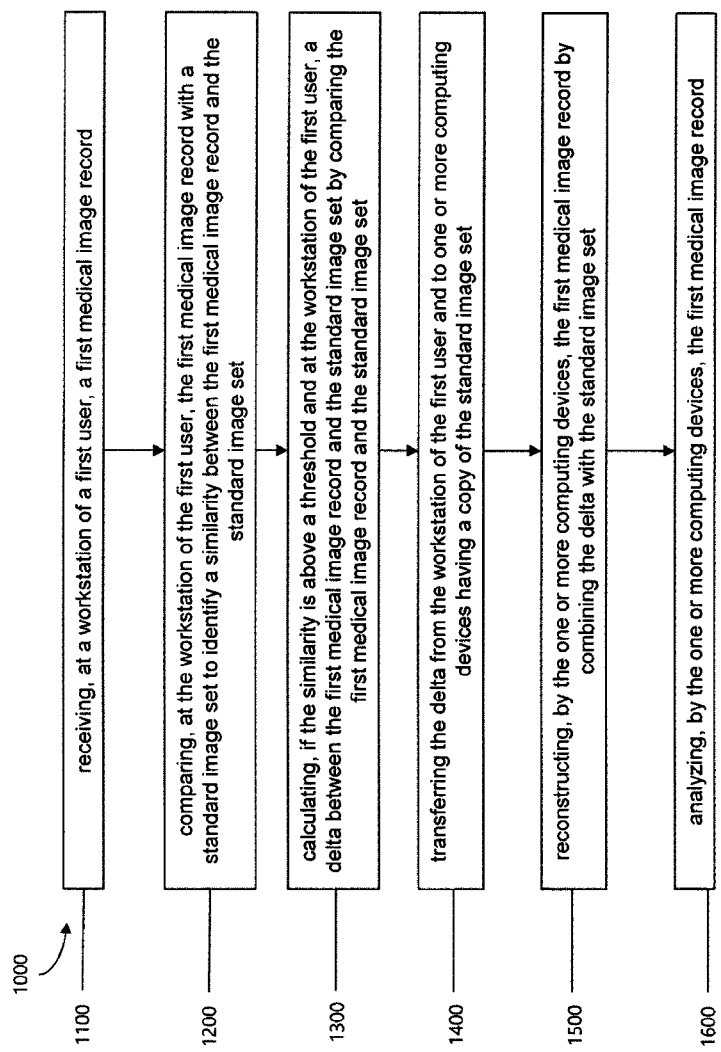
FIG. 6 is a flow chart for a method for remote analysis of one or more medical image records in accordance with the disclosed subject matter.

FIG. 6 illustrates an example method 1000 for remote analysis of one or more medical image records. The method can begin at step 1100, where the method includes receiving, at a workstation of a first user, a first medical image record. At step 1200, the method can include comparing, at the workstation of the first user, the first medical image record with a standard image set to identify a similarity between the first medical image record and the standard image set. At step 1300 the method can include calculating, if the similarity is above a threshold and at the workstation of the first user, a delta between the first medical image record and the standard image set by comparing the first medical image record and the standard image set. At step 1400 the method can include transferring the delta from the workstation of the first user and to one or more computing devices having a copy of the standard image set. At step 1500, the method can include reconstructing, by the one or more computing devices, the first medical image record by combining the delta with the standard image set. At step 1600 the method can include analyzing, by the one or more computing devices, the first medical image record. In accordance with the disclosed subject matter, the method can repeat one or more steps of the method of FIG. 6, where appropriate. Although this disclosure describes and illustrates particular steps of the method of FIG. 6 as occurring in a particular order, this disclosure contemplates any suitable steps of the method of FIG. 6 occurring in any suitable order. Moreover, although this disclosure describes and illustrates an example method for remote analysis of one or more medical image records including the particular steps of the method of FIG. 6, this disclosure contemplates any suitable method for remote analysis of one or more medical image records including any suitable steps, which can include all, some, or none of the steps of the method of FIG. 6, where appropriate. Furthermore, although this disclosure describes and illustrates particular components, devices, or systems carrying out particular steps of the method of FIG. 6, this disclosure contemplates any suitable combination of any suitable components, devices, or systems carrying out any suitable steps of the method of FIG. 6.

As described above in connection with certain embodiments, certain components, e.g., server 10 and workstation 60, can include a computer or computers, processor, network, mobile device, cluster, or other hardware to perform various functions. Moreover, certain elements of the disclosed subject matter can be embodied in computer readable code which can be stored on computer readable media and which when executed can cause a processor to perform certain functions described herein. In these embodiments, the computer and/or other hardware play a significant role in permitting the system and method for displaying medical image records. For example, the presence of the computers, processors, memory, storage, and networking hardware provides the ability to display medical image records in a more efficient manner. Moreover, the display of medical image records, cannot be accomplished with pen or paper, as such information is received over a network in electronic form.

The subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or may be included in, one or more separate physical components or media (e.g., multiple CDs, disks, or other storage devices).

The term "processor" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA or an ASIC. The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program can, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA or an ASIC.

Processors suitable for the execution of a computer program can include, by way of example and not by way of limitation, both general and special purpose microprocessors. Devices suitable for storing computer program instructions and data can include all forms of non-volatile memory, media and memory devices, including by way of example but not by way of limitation, semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

Additionally, as described above in connection with certain embodiments, certain components can communicate with certain other components, for example via a network, e.g., a local area network or the internet. To the extent not expressly stated above, the disclosed subject matter is intended to encompass both sides of each transaction, including transmitting and receiving. One of ordinary skill in the art will readily understand that with regard to the features described above, if one component transmits, sends, or otherwise makes available to another component, the other component will receive or acquire, whether expressly stated or not.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A method for remote analysis of one or more medical image records, comprising:
   receiving, at a workstation of a first user, a first medical image record having a first amount of data;
   comparing, at the workstation of the first user, the first medical image record with each standard image of a standard image set to identify a similarity between the first medical image record and each of the standard images, wherein the standard image set comprises at least two standard images of an anatomical feature, each standard image comprising a generic image of the anatomical feature generated by a machine learning algorithm from a review of at least 1000 images of the anatomical feature including normal and abnormal images of the anatomical feature, each standard image associated with a respective index number;
   calculating, if at least one respective similarity is above a threshold and at the workstation of the first user, a delta between the first medical image record and at least one of the standard images with the similarity above the threshold by comparing the first medical image record and the at least one standard with the similarity above the threshold, the delta having a second amount of data, the second amount of data being less than the first amount of data;
   transferring the delta from the workstation of the first user and to one or more computing devices having a copy of the standard image set;
   transferring a plurality of index numbers from the workstation of the first user and to the one or more computing device, wherein each of the plurality of index numbers is associated with a respective standard image;
   combining, by the one or more computing devices, the delta and the at least one standard image with similarity above the threshold;
   reconstructing, by the one or more computing devices, the first medical image record using the combination of the delta and the at least one standard image with similarity above the threshold to form a first reconstructed medical image record, the first reconstructed medical image record being identical to the first medical image record; and
   analyzing, by the one or more computing devices, the first reconstructed medical image record.

2. The method of claim 1, wherein the first medical image record comprises one or more Digital Imaging and Communications in Medicine ("DICOM") Service-Object Pair ("SOP") Instances.

3. The method of claim 1, further comprising providing an alert to the user if the similarity is below a threshold.

4. The method of claim 1, wherein comparing the first medical image record with each standard image comprises determining that the first medical image record and the standard image set each correspond with a similar anatomical feature.

5. The method of claim 1, wherein analyzing the first reconstructed medical image record comprises determining a medical diagnosis.

6. The method of claim 5, further comprising sending an alert to the workstation of the first user if the medical diagnosis is abnormal.

7. The method of claim 1, wherein analyzing the first reconstructed medical image record comprises using an artificial intelligence ("AI") engine stored on the one or more computing devices.

8. The method of claim 1, further comprises sending, from the one or more computing devices and to the workstation of the first user, the analysis of the first medical image record.

9. One or more computer-readable non-transitory storage media embodying software that is operable when executed to:
  receive, at a workstation of a first user, a first medical image record having a first amount of data;
  compare, at the workstation of the first user, the first medical image record with each standard image of a standard image set to identify a similarity between the first medical image record and each of the standard images, wherein the standard image set comprises at least two standard images of an anatomical feature, each standard image comprising a generic image of the anatomical feature generated by a machine learning algorithm from a review of at least 1000 images of the anatomical feature including normal and abnormal images of the anatomical feature, each standard image associated with a respective index number;
  identify, if at least one respective similarity is above a threshold and at the workstation of the first user, a delta between the first medical image record and at least one of the standard images with the similarity above the threshold by comparing the first medical image record and the at least one standard image with the similarity above the threshold, the delta having a second amount of data, the second amount of data being less than the first amount of data;
  transfer the delta from the workstation of the first user and to one or more computing devices having a copy of the standard image set;
  transfer a plurality of index numbers from the workstation of the first user and to the one or more computing device, wherein each of the plurality of index numbers is associated with a respective standard image;
  combine, by the one or more computing devices, the delta and the first at least one standard image with similarity above the threshold;
  reconstruct, by the one or more computing devices, the first medical image record using the combination of the delta and the at least one standard image with similarity above the threshold to form a first reconstructed medical image record, the first reconstructed medical image record being identical to the first medical image record; and
  analyze, by the one or more computing devices, the first reconstructed medical image record.

10. The media of claim 9, wherein the first medical image record comprises one or more Digital Imaging and Communications in Medicine ("DICOM") Service-Object Pair ("SOP") instances.

11. The media of claim 9, wherein the software is further operable to provide an alert to the user if the similarity is below a threshold.

12. The media of claim 9, wherein comparing the first medical image record with each standard image comprises determining that the first medical image record and the standard image set each correspond with a similar anatomical feature.

13. The media of claim 9, wherein analyzing the first reconstructed medical image record comprises determining a medical diagnosis.

14. The media of claim 13, further comprising sending an alert to the workstation of the first user if the medical diagnosis is abnormal.

15. The media of claim 9, wherein analyzing the first reconstructed medical image record comprises using an artificial intelligence ("AI") engine stored on the one or more computing devices.

16. The media of claim 9, further comprises sending, from the one or more computing devices and to the workstation of the first user, the analysis of the first medical image record.

17. A system comprising: one or more processors; and a memory coupled to the processors comprising instructions executable by the processors, the processors being operable when executing the instructions to:
  receive, at a workstation of a first user, a first medical image record having a first amount of data;
  compare, at the workstation of the first user, the first medical image record with each standard image of a standard image set to identify a similarity between the first medical image record and each of the standard images, wherein the standard image set comprises at least two standard images of an anatomical feature, each standard image comprising a generic image of the anatomical feature generated by a machine learning algorithm from a review of at least 1000 images of the anatomical feature including normal and abnormal images of the anatomical feature, each standard image associated with a respective index number;
  identify, if at least one respective similarity is above a threshold and at the workstation of the first user, a delta between the first medical image record and at least one of the standard images with the similarity above the threshold by comparing the first medical image record and the at least one standard image with the similarity above the threshold, the delta having a second amount of data, the second amount of data being less than the first amount of data;
  transfer the delta from the workstation of the first user and to one or more computing devices having a copy of the standard image set;
  transfer a plurality index numbers from the workstation of the first user and to the one or more computing device, wherein each of the plurality of index numbers is associated with a respective standard image;
  combine, by the one or more computing devices, the delta and the at least one standard image with similarity above the threshold;
  reconstruct, by the one or more computing devices, the first medical image record using the combination of the delta and the at least one standard image with similarity above the threshold to form a first reconstructed medical image record, the first reconstructed medical image record being identical to the first medical image record; and
  analyze, by the one or more computing devices, the first reconstructed medical image record.

18. A system for remote analysis of one or more medical image records, comprising:
a workstation including
a processor, including a pre-processing AI engine for processing a first medical image record, and
a memory storing a first copy of a standard image set, wherein the standard image set comprises at least two standard images of an anatomical feature, each standard image comprising a generic image of the anatomical feature generated by a machine learning algorithm from a review of at least 1000 images of the anatomical feature including normal and abnormal images of the anatomical feature, each standard image associated with a respective index number; and
one or more computing devices operationally coupled to the workstation, the one or more computing devices including
an AI engine, and
an AI engine storage storing a second copy of the standard image set; wherein the system is configured to
compare, at the workstation, a first medical image record with each standard image of the first copy of the standard image set to identify a similarity between the first medical image record and each of the standard images, wherein the first medical image record has a first amount of data;
calculate, if the similarity is above a threshold and at the workstation, a delta between the first medical image record and the first standard image by comparing the first medical image record and the first standard image, the delta having a second amount of data, the second amount of data being less than the first amount of data;
transfer the delta from the workstation and to the one or more computing devices;
transfer a plurality of index numbers from the workstation and to the one or more computing devices, wherein each of the plurality of index numbers is associated with a respective standard image;
combine, by the one or more computing devices, the delta and the at least one standard image with similarity above the threshold;
reconstruct, by the one or more computing devices, the first medical image record using the combination of the delta and the at least one standard image with similarity above the threshold to form a first reconstructed medical image record, the first reconstructed medical image record being identical to the first medical image record.

19. The system of claim 18, wherein the workstation further comprises a transceiver for sending a delta to the server.

20. The system of claim 19, wherein the delta is calculated by the pre-processing AI engine.

21. The system of claim 18, wherein the workstation further comprises a graphical user interface.

22. The system of claim 18, wherein the one or more computing devices further comprise a server processor.

23. The system of claim 18, further comprising an imaging modality operationally coupled to the workstation to send the first medical image record from the imaging modality to the workstation.

* * * * *